US012605570B2

(12) United States Patent
Alam et al.

(10) Patent No.: US 12,605,570 B2
(45) Date of Patent: Apr. 21, 2026

(54) APPARATUS AND METHOD FOR ULTRASOUND SPINAL CORD STIMULATION

(71) Applicant: THE HONG KONG POLYTECHNIC UNIVERSITY, Hong Kong (CN)

(72) Inventors: Md. Monzurul Alam, Hong Kong (CN); Yongping Zheng, Hong Kong (CN)

(73) Assignee: THE HONG KONG POLYTECHNIC UNIVERSITY, Hong Kong (CN)

( * ) Notice: Subject to any disclaimer, the term of this patent is extended or adjusted under 35 U.S.C. 154(b) by 32 days.

(21) Appl. No.: 18/959,838

(22) Filed: Nov. 26, 2024

(65) Prior Publication Data

US 2025/0121218 A1 Apr. 17, 2025

Related U.S. Application Data

(62) Division of application No. 16/623,816, filed as application No. PCT/CN2017/089401 on Jun. 21, 2017, now Pat. No. 12,214,221.

(51) Int. Cl.
| | |
|---|---|
| *A61N 7/00* | (2006.01) |
| *A61B 8/00* | (2006.01) |
| *A61K 9/00* | (2006.01) |
| *A61K 35/12* | (2015.01) |

(52) U.S. Cl.
CPC .............. *A61N 7/00* (2013.01); *A61B 8/4494* (2013.01); *A61K 9/0019* (2013.01); *A61K*

35/12 (2013.01); *A61N 2007/0026* (2013.01); *A61N 2007/0078* (2013.01); *A61N 2007/0095* (2013.01)

(58) Field of Classification Search
CPC .............. A61N 7/00; A61N 2007/0026; A61N 2007/0078; A61N 2007/0095; A61B 8/4494; A61B 8/4227; A61B 8/0875; A61K 9/0019; A61K 35/12
See application file for complete search history.

(56) References Cited

U.S. PATENT DOCUMENTS

| | | | |
|---|---|---|---|
| 5,694,936 A | 12/1997 | Fujimoto et al. | |
| 8,348,846 B2 * | 1/2013 | Gunther ............... | A61B 8/4245 |
| | | | 600/443 |
| 2009/0112281 A1 | 4/2009 | Miyazawa et al. | |
| 2011/0009734 A1 | 1/2011 | Foley et al. | |
| 2012/0101366 A1 | 4/2012 | Ruohonen et al. | |
| 2012/0259252 A1 | 10/2012 | Thorn-Leeson et al. | |
| 2013/0178765 A1 | 7/2013 | Mishelevich | |

(Continued)

*Primary Examiner* — Hien N Nguyen
(74) *Attorney, Agent, or Firm* — S&F/WEHRW

(57) ABSTRACT

A method for ultrasound stimulation of spinal cord, the method comprising at least two stimulation cycles, each comprising the steps of: a) obtaining a first real-time spinal cord using a first set of ultrasound transducers; b) selecting a pre-determined stimulation area of the spinal cord from the first real-time spinal cord; c) calculating the position and orientation of the selected stimulation area relative to a second set of ultrasound transducers; and d) stimulating the selected stimulation area of the spinal cord at the calculated relative position and orientation using the second set of ultrasound transducers.

16 Claims, 5 Drawing Sheets

(56) References Cited

U.S. PATENT DOCUMENTS

| | | | |
|---|---|---|---|
| 2015/0133785 A1* | 5/2015 | Schlenger | G16H 50/30 |
| | | | 600/443 |
| 2016/0045740 A1 | 2/2016 | Rezai et al. | |
| 2017/0106208 A1 | 4/2017 | Gauthier et al. | |
| 2018/0264291 A1 | 9/2018 | Rem-Bronneberg et al. | |
| 2019/0184206 A1 | 6/2019 | Nazer et al. | |

* cited by examiner

1

1

APPARATUS AND METHOD FOR ULTRASOUND SPINAL CORD STIMULATION

CROSS-REFERENCE TO RELATED APPLICATIONS

This application is a divisional patent application of U.S. patent application Ser. No. 16/623,816, filed on Dec. 18, 2019, which is a national phase entry application of PCT international application number PCT/CN2017/089401, filed on Jun. 21, 20217, the disclosures of which are incorporated herein by reference.

FIELD OF THE INVENTION

The present disclosure generally relates to an apparatus and method for spinal cord stimulation useful for functional rehabilitation after paralysis and, in particular to an apparatus and method for ultrasound image guided ultrasound spinal cord neuromodulation.

BACKGROUND OF THE INVENTION

The mammalian spinal cord is composed of specialized neural networks (SNN), capable of controlling different functions of daily living. Special interneurons are located in the cervical and lumbar enlargements of the spinal cord. They form neuronal networks that play an important role in the neuromuscular activities involved in reaching, grasping, breathing, coughing, speaking, standing, stepping, bladder and bowl voiding, postural control etc. It is believed that all mammals, including humans, have SNN in the cervical and lumbosacral spinal cord regions. The SNN located at the lumbosacral spinal cord organizes rhythmic leg movements essential for locomotion, such as walking.

Normally, the activity of SNN is regulated supraspinally and by peripheral sensory inputs. In case of disruption of the connection between the brain and the spinal cord (e.g. as a result of an injury or disease), locomotor function can still be enabled by external stimuli such as electrical stimulation to the lumbosacral SNN. Therefore, it is possible to restore or improve the walking function of paraplegic patients by neuromodulation, in particular by spinal cord stimulation of the SNN.

There have been several methods of stimulating the spinal cord neural circuits. These include both electrical and magnetic stimulations. Spinal stimulations via electric voltage or current are mainly of three kinds: intraspinal stimulation (IS), epidural stimulation (ES) and transcutaneous stimulation (TS). Among these electrical stimulating methods, intraspinal stimulation and epidural stimulation are generally invasive. They are delivered through intraspinal penetrating electrodes and epidurally placed electrodes respectively. For transcutaneous stimulation, the electrical stimulation is delivered through transcutaneous surface electrodes. In other words, it is non-invasive. The magnetic stimulating method is generally non-invasive. The magnetic stimulation utilizes conventional transcranial magnetic stimulation (TMS) coil placed on the spine.

Researchers and medical practitioners have found it difficult to strike a balance between non-invasiveness and effectiveness. Invasive stimulating methods allow more precise localization of stimulation. Intraspinal stimulating method is capable of targeting areas at micrometer range. It can deliver stimulation to any area including dorsal and ventral structures of the spinal cord. The less invasive epidural stimulating method can achieve a precision at millimeter range, and the dorsal stimulation can go no deeper than dorsal structures (i.e. it cannot reach ventral structure). It is important to note that it is not feasible to make epidural implant to the ventral surface of the spinal cord due to the very complex and risky surgical procedure. The non-invasive magnetic stimulating method has a centimeter resolution and the transcutaneous stimulating method can only perform widespread non-specific stimulation that activates the spinal cord through afferent pathway. Better localization of stimulation generally means more effective rehabilitation. It is suggested that body weight-bearing standing is possible via intraspinal stimulation in the spinal cord. On the other hand, epidural stimulation is conventionally found effective for pain suppression, but recent studies have demonstrated its potential on rehabilitation after paralysis. Transcutaneous stimulation alone is found no more effective than inducing rhythmic activities of legs in gravity neutral position and in robotic driven body-weight supported upright position. Finally, studies show magnetic stimulation can only induce very limited walking like pattern in body-weight supported upright position.

In connection with the effectiveness of invasive stimulating methods, there are issues of surgery, bio-compatibility and induced plasticity. Both intraspinal and epidural electrical stimulations require a surgical laminectomy of the spine for implantation of stimulation electrodes. There is another incision needs to be made at the back of patient to implant the stimulator. The implanted electrodes and the stimulator remain functional for usually a few years, so frequent surgery may be needed to replace the electrodes, the battery, or the stimulator. Furthermore, many paralyzed patients may not be able to be included in these treatments due to incapability to receive surgeries. These issues are major barriers of using invasive (intraspinal and epidural) stimulation method for functional rehabilitation after paralysis.

BRIEF SUMMARY OF THE INVENTION

A need therefore exists for a novel neuromodulation technique that eliminates or diminishes the disadvantages and problems described above. In particular, an ideal intervention should be both non-invasive and sufficiently specific.

Provided is a method for ultrasound stimulation of a spinal cord, the method comprising at least two stimulation cycles, each comprising the steps of: a) obtaining a first real-time spinal cord image using a first set of ultrasound transducers; b) selecting a pre-determined stimulation area of the spinal cord from the first real-time spinal cord image; c) calculating the position and orientation of the selected stimulation area relative to a second set of ultrasound transducers; and d) stimulating the selected stimulation area of the spinal cord at the calculated relative position and orientation using the second set of ultrasound transducers.

In certain embodiments, each stimulation cycle further comprising the steps of: e) at the same time of or after step d), obtaining a second real-time spinal cord image using the first set of ultrasound transducers; f) recognizing an actual stimulation area of the spinal cord from the second real-time spinal cord image; and g) adjusting at least one of steps b) to d) based on a difference between the actual stimulation area and the pre-determined stimulation area.

In certain embodiments, the difference comprises difference in location, contour and/or size between the actual stimulation area and the pre-determined stimulation area.

In certain embodiments, the difference comprises an evoked response of the muscle at the actual stimulation area.

In certain embodiments, adjusting step b) comprises optimizing an image recognition algorithm for selecting the pre-determined stimulation area of the spinal cord from the first real-time spinal cord image.

In certain embodiments, adjusting step c) comprises compensating the calculation of the position and orientation of the selected stimulation area relative to the second set of ultrasound transducers.

In certain embodiments, adjusting step d) comprises adjusting at least one of focus point, focus area, intensity and frequency of the ultrasound beam, and duty cycle, repetition rate and duration of the stimulation cycle.

In certain embodiments, the second real-time spinal cord image is taken by the first set of ultrasound transducers at a rate over 2,000 frames per second.

In certain embodiments, each stimulation cycle further comprising the steps of: h) at the same time of or after step d), collecting a signal representing muscle contraction from muscle innervated from the pre-determined stimulation area of the spinal cord; and i) adjusting at least one of steps b) to d) based on the signal.

In certain embodiments, the signal comprises at least one of electromyography, sonomyography, mechanomyography, or electroneurography signals.

In certain embodiments, adjusting step b) comprises optimizing an image recognition algorithm for selecting the pre-determined stimulation area of the spinal cord from the first real-time spinal cord image.

In certain embodiments, adjusting step c) comprises compensating the calculation of the position and orientation of the selected stimulation area relative to the second set of ultrasound transducers.

In certain embodiments, adjusting step d) comprises adjusting at least one of focus point, focus area, intensity and frequency of the ultrasound beam, and duty cycle, repetition rate and duration of the stimulation cycle.

In certain embodiments, step b) comprises the step of selecting multiple pre-determined stimulation areas of the spinal cord, and step d) comprises the step of simultaneous multifocal stimulation of the multiple selected stimulation areas of the spinal cord, so as to simultaneously activate multiple muscle groups required for a motion function.

In certain embodiments, in step d) an ultrasound beam of the second set of transducers reaches the selected stimulation area of the spinal cord by passing through a gap between vertebral bones and the lamina.

Provided is a method for ultrasound stimulated rehabilitation of a spinal cord injury or disease, the method comprising: i) injecting stem cells in a pre-determined area of the spinal cord, ii) performing at least two stimulation cycles, each comprising the steps of: a) obtaining a first real-time spinal cord image using a first set of ultrasound transducers; b) selecting the stem cells or the pre-determined area of the spinal cord with stem cells from the first real-time spinal cord image; c) calculating the position and orientation of the stem cells or the selected area of the spinal cord with stem cells relative to a second set of ultrasound transducers; and d) stimulating the stem cells or the selected pre-determined damaged area of the spinal cord at the calculated relative position and orientation using the second set of ultrasound transducers.

In certain embodiments, each stimulation cycle further comprising the steps of: e) at the same time of or after step d), obtaining a second real-time spinal cord image using the first set of ultrasound transducers; f) recognizing the injected stem cells form the second real-time spinal cord image; and g) adjusting at least one of steps b) to d) based on an evoked response of the stem cells.

In certain embodiments, adjusting step b) comprises optimizing an image recognition algorithm for selecting the stem cells or the pre-determined area of the spinal cord with stem cells from the first real-time spinal cord image.

In certain embodiments, adjusting step c) comprises compensating the calculation of the position and orientation of the stem cells or the selected area of the spinal cord with stem cells relative to the second set of ultrasound transducers.

In certain embodiments, adjusting step d) comprises adjusting at least one of focus point, focus area, intensity and frequency of the ultrasound beam, and duty cycle, repetition rate and duration of the stimulation cycle.

Provided is a method for volitional triggering of a motor action, the method comprising: i) receiving a brain signal representing an intended motor action, ii) determining a stimulation area of the spinal cord with reference to an established functional mapping of the spinal cord; iii) performing at least two stimulation cycles, each comprising the steps of: a) obtaining a first real-time spinal cord image using a first set of ultrasound transducers; b) selecting the determined stimulation area of the spinal cord from the first real-time spinal cord image; c) calculating the position and orientation of the selected stimulation area relative to a second set of ultrasound transducers; and d) stimulating the selected stimulation area of the spinal cord at the calculated relative position and orientation using the second set of ultrasound transducers.

In certain embodiments, each stimulation cycle further comprises the steps of: e) at the same time of or after step d), obtaining a second real-time spinal cord image using the first set of ultrasound transducers; f) recognizing an actual stimulation area of the spinal cord from the second real-time spinal cord image; and g) adjusting at least one of steps b) to d) based on a difference between the actual stimulation area and the determined stimulation area.

In certain embodiments, the difference comprises difference in location, contour and/or size between the actual stimulation area and the determined stimulation area.

In certain embodiments, the difference comprises an evoked response of the muscle at the actual stimulation area.

In certain embodiments, adjusting step b) comprises optimizing an image recognition algorithm for selecting the determined stimulation area of the spinal cord from the first real-time spinal cord image.

In certain embodiments, adjusting step c) comprises compensating the calculation of the position and orientation of the selected stimulation area relative to the second set of ultrasound transducers.

In certain embodiments, adjusting step d) comprises adjusting at least one of focus point, focus area, intensity and frequency of the ultrasound beam, and duty cycle, repetition rate and duration of the stimulation cycle.

In certain embodiments, the method further comprises the steps of: h) at the same time of or after step d), collecting a signal representing muscle contraction from muscle innervated from the determined stimulation area of the spinal cord; and i) adjusting at least one of steps b) to d) based on the signal.

In certain embodiments, the signal comprises at least one of electromyography, sonomyography, mechanomyography, or electroneurography signals.

In certain embodiments, adjusting step b) comprises optimizing an image recognition algorithm for selecting the determined stimulation area of the spinal cord from the first real-time spinal cord image.

In certain embodiments, adjusting step c) comprises compensating the calculation of the position and orientation of the selected stimulation area relative to the second set of ultrasound transducers.

In certain embodiments, adjusting step d) comprises adjusting at least one of focus point, focus area, intensity and frequency of the ultrasound beam, and duty cycle, repetition rate and duration of the stimulation cycle.

In certain embodiments, step ii) comprises the step of determining multiple stimulation areas of the spinal cord with reference to the established functional mapping of the spinal cord, step b) comprises the step of selecting the multiple determined stimulation areas of the spinal cord, and step d) comprises the step of simultaneous multifocal stimulation of the multiple selected stimulation areas of the spinal cord so as to simultaneously activate multiple muscle groups required for a motion function.

In certain embodiments, the brain signal comprises at least one of electroencephalogram (EEG), electrocorticography (ECoG), near-infrared spectroscopy, or brain vessel blood flow signal.

Provided is an apparatus for ultrasound stimulation of a spinal cord, the apparatus comprising: an imaging module, the imaging module comprises a first set of ultrasound transducers configured to obtain real-time spinal cord images; an image recognition module, the image recognition module is configured to select a pre-determined stimulation area of the spinal cord from the real-time spinal cord images, and to calculate the position and orientation of the selected stimulation area relative to a second set of ultrasound transducers; a stimulating module, the stimulating module comprises the second set of ultrasound transducers configured to stimulate the selected pre-determined stimulation area of the spinal cord at the calculated relative position and orientation; and a control module, the control module is configured to coordinate the imaging module, the image recognition module and the stimulating module to operate in at least two stimulation cycles such that, in each of the at least two stimulation cycles, a first real-time spinal cord image is obtained by the imaging module, the pre-determined stimulation area is selected and the position and orientation of the selected stimulation area relative to the second set of transducers is calculated by the image recognition module, and the stimulating module applies an ultrasound stimulation to the selected stimulation area of the spinal cord.

In certain embodiments, the first set of ultrasound transducers and the second set of ultrasound transducers are the same set of ultrasound transducers arranged within a transducer array.

In certain embodiments, the transducer array is flexible.

In certain embodiments, the first and/or second sets of ultrasound transducers are arranged in one or two dimensions as a transducer array.

In certain embodiments, the first and second sets of transducers are located on a skin surface of patient in use.

In certain embodiments, the control module is further configured to coordinate the imaging module, the image recognition module and the stimulating module such that, in each of the at least two stimulation cycles, at the same time of or after ultrasound stimulation is applied to the selected stimulation area of the spinal cord by the stimulating module, the imaging module obtains a second real-time spinal cord image, the recognition module recognizes an actual stimulation area of the spinal cord form the second real-time spinal cord image, and the control module adjusts the recognition module and/or the stimulating module based on a difference between the actual stimulation area and the pre-determined stimulation area.

In certain embodiments, the difference comprises difference in location, contour and/or size between the actual stimulation area and the pre-determined stimulation area.

In certain embodiments, the difference comprises an evoked response of the muscle at the actual stimulation area.

In certain embodiments, adjusting the recognition module comprises at least one of (1) optimizing an image recognition algorithm of the recognition module for selecting the pre-determined stimulation area of the spinal cord from the first real-time spinal cord image; and (2) compensating the calculation of the position and orientation of the selected stimulation area relative to the second set of ultrasound transducers.

In certain embodiments, adjusting the stimulating module comprises adjusting at least one of focus point, focus area, intensity and frequency of the ultrasound beam, and duty cycle, repetition rate and duration of the stimulation cycle.

In certain embodiments, the apparatus further comprises a feedback module, the feedback module is configured to receive a signal representing muscle contraction from muscle innervated from the pre-determined stimulation area of the spinal cord, and the control module adjusts the recognition module and/or the stimulating module based on the signal.

In certain embodiments, the signal comprises at least one of electromyography, sonomyography, mechanomyography, or electroneurography signals.

In certain embodiments, adjusting the recognition module comprises at least one of (1) optimizing an image recognition algorithm of the recognition module for selecting the pre-determined stimulation area of the spinal cord from the first real-time spinal cord image; and (2) compensating the calculation of the position and orientation of the selected stimulation area relative to the second set of ultrasound transducers.

In certain embodiments, adjusting the stimulating module comprises adjusting at least one of focus point, focus area, intensity and frequency of the ultrasound beam, and duty cycle, repetition rate and duration of the stimulation cycle.

In certain embodiments, the apparatus further comprises a stem cell injection module, the stem cell injection module is configured to inject stem cells in the pre-determined stimulation area of the spinal cord so that ultrasound stimulation can be applied to the stem cells at the pre-determined stimulation area of the spinal cord.

In certain embodiments, the apparatus further comprising a brain signal receiving module in communication with the control module, the brain signal receiving module receives a brain signal representing an intended motor action and sends it to the control module, the control module determines a stimulation area with reference to an established functional mapping of the spinal cord so that ultrasound stimulation can be applied to the determined stimulation area to induce the intended motor action.

These and other aspects, features and advantages of the present disclosure will become more fully apparent from the following brief description of the drawings, the drawings, the detailed description of certain embodiments and appended claims.

BRIEF DESCRIPTION OF THE DRAWINGS

The appended drawings contain figures of certain embodiments to further illustrate and clarify the above and other aspects, advantages and features of the present disclosure. It will be appreciated that these drawings depict only certain embodiments of the disclosure and are not intended to limit its scope. The disclosure will be described and explained with additional specificity and detail through the use of the accompanying drawings in which.

DETAILED DESCRIPTION OF THE EMBODIMENTS

Figure 1:
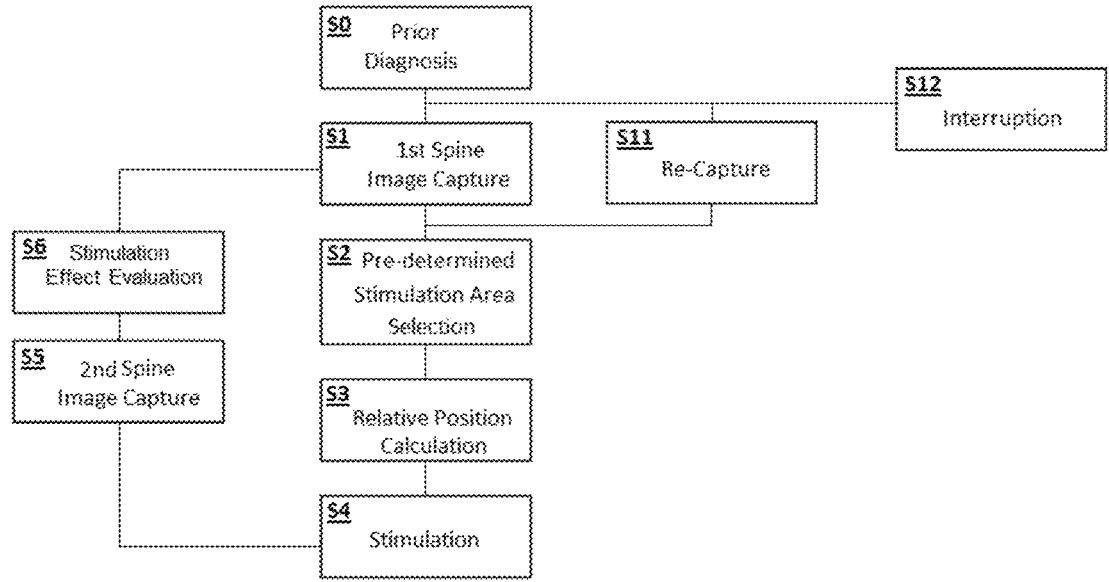
FIG. 1 illustrates a method for ultrasound stimulation of spinal cord according to certain embodiments of the present disclosure.

The present disclosure is generally directed towards rehabilitation in relation to paralysis resulted from spinal cord injury or disease (such as stroke) using ultrasound image guided ultrasound stimulations. The principles of the present disclosure, however, are not limited to such use. It will be understood that, in light of the present disclosure, the apparatus and method disclosed herein can be successfully used in connection with treatment of other diseases via ultrasound stimulations (such as pain suppression), or with other applications where ultrasound application is needed.

Additionally, to assist in the description, certain embodiments are introduced in detail. It will be appreciated that modifications can be made in a variety of situations to perform a number of different functions. In addition, the drawings can be scaled and may illustrate various configurations, arrangements, aspects and features. It will be appreciated, however, the modules can have other suitable shapes, sizes, configurations and arrangements depending, for example, upon the intended use of the apparatus. Further, the reasonable modification can include any suitable number or combination, splitting or rearrangement of components, aspects, features and the like. In addition, unless specified otherwise, 'an image' used herein can represent one single image or a series of images. Likewise, 'an area' can represent one single area or a plurality of areas. When stimulation is applied to an area of spinal cord, it may be applied to different types of tissues within the spinal cord, such as but not limited to tracts, neurons, muscles, fibers and cells. The target of stimulation is determined in accordance with medi-cal opinions and is not intended to limit the scope of the present disclosure. A detailed description of exemplary embodiments now follows.

The present disclosure provides an apparatus and method for spinal cord ultrasound stimulation for the purpose of rehabilitation of patients with paralyzing injury or disease. Patients generally refer to human beings, but other mammals are also included. The patient can receive periodic treatment with the method disclosed herewith in an institution, or he or she can receive such treatment via portable apparatus.

Before treatment, a patient with spinal cord injury or disease has usually been diagnosed and already received medical advice on the spinal cord muscles and/or spinal cord areas to be stimulated for rehabilitation. In certain embodiments, the diagnosis will directly find out the muscles or areas of the spinal cord that are impaired. In other embodiments, the diagnosis comprises finding out the extent of loss of motor function and determining the muscles or areas that are impaired with reference to an established functional mapping of spinal cord.

As discussed earlier, the present disclosure has found it important to localize the stimulation accurately. The reason that invasive stimulating methods are more effective is largely due to their better localization of stimulation. The precise activation of efferent motor circuits is essential for the movement restoration. It is crucial that the stimulation should be directed to the neural circuits in the spinal cord to generate an action potential, and the action potential eventually propagate through the ventral horn of the spinal cord to the periphery and produces muscle contraction. As such, a consequence of spinal cord stimulation generates a train of action potentials that produce coordinated muscle contractions and induces movement. On the other hand, stimulation of the wrong site is not effective and has potential side effects. It is also important to note that sub-threshold ultrasound stimulation may lower the excitability of the spinal cord neurocircuits and let the action potential to propagate to the periphery and activate the paretic muscle which otherwise remains nonfunctional.

As the muscles and/or the areas of the spinal cord to be stimulated are pre-determined in prior diagnosis, there are several possible sources leading to inaccurate application of ultrasound stimulation. In the first place, whether the apparatus is a platform or wearable form, it is likely that the patient will have dynamic changes of posture or motions during treatment, and the location and curvature of spine may consequently change. Despite the target stimulation area remains the same, its spatial position and orientation relative to the apparatus may have well changed during treatment. In this regard, a once and for all pre-selection of the stimulation area may not be effective for the subsequent stimulations. Secondly, the inaccuracy may come from selection of the pre-determined stimulation area. Whether it be manual selection or selection by image recognition algorithm, there is chance of error in the selection process. As such, the stimulation area selected may not accurately correspond with the muscles or areas intended to be stimulated. In other circumstances, the error may come from the prior diagnosis so that the muscles or areas of the spinal cord to be stimulated are wrongly determined in the first place. Thirdly, even where the stimulation area is accurately selected, ultrasound stimulation may still be applied to places other than the stimulation area for various reasons, in particular the error may come from the determination of relative position and orientation between the target stimulation area and the stimulation transducers; or the ultrasound stimulation may be applied with parameters that are not optimal.

To address at least some of the above issues, the present disclosure has envisaged an ultrasound image guided ultrasound stimulation of the spinal cord. In the present disclosure, the apparatus works in a real-time mode. The real-time mode generally means the spinal cord stimulation is divided into many stimulation cycles each comprising at least one imaging process and one stimulation process. Each stimulation cycle may lasts a few minutes, such as 1, 2, 3, 4, 5, 6, 7, 8, 9 or 10 minutes; or a few seconds, such as 1, 2, 3, 4, 5, 10, 15, 20, 25, 30, 35, 40, 45, 50, 55 or 60 seconds; or within a second. A first real-time spinal cord image is captured in a first imaging process and is used for guiding the stimulation process that immediately follows the first imaging process in the same stimulation cycle. As such, immediately before the stimulation process in each cycle, the first real-time spinal cord image is obtained in the first imaging process, and stimulation areas of the spinal cord corresponding with the pre-determined stimulation muscles or areas are selected from the first real-time spinal cord image to make sure the same pre-determined stimulation muscles/areas are chosen for immediately subsequent stimulation process. There is essentially no time lapse between the first imaging process and the stimulation process. This real-time mode is believed to be capable of compensating the possible changes of posture or motions of the patient during treatment.

During operation of the apparatus, it can also involve a feedback to the ultrasound image guided stimulation. In certain embodiments, the first imaging process and/or the stimulation process of the ultrasound image guided stimulation can benefit from the feedback. At the same time of or immediately after the stimulation process in each stimulation cycle, a second real-time spinal cord image is obtained in a second imaging process, from which a difference between the intended stimulation and the actual stimulation is determined. In certain embodiments, the location, contour and/or size of the actual stimulation area is determined. Ideally the actual stimulation area coincides with the pre-determined stimulation area but there can be occasions they do not match. As discussed earlier, this may be due to the selected stimulation area does not exactly correspond with the pre-determined stimulation area, or despite the accurate selection, the ultrasound stimulation is not applied accurately to the selected stimulation area. In that case, the difference in location, contour and/or size between the actual stimulation area and the pre-determined stimulation area is calculated. This information can be relied on to adjust the first imaging process and/or the stimulation process in the next stimulation cycle.

The difference between the intended stimulation and the actual stimulation can also be obtained by observing, in the second imaging process, an evoked response of the muscles or other tissues at the actual stimulation area. For this purpose, a second real-time spinal cord image does not necessarily mean one single image. It can comprise a series of images to enable temporal analysis. As discussed earlier, not only should the stimulation be applied to the right place, it should also be applied in the right manner. Parameters, such as the focus point, focus area, intensity and frequency of the ultrasound beam; and the duty cycle, repetition rate and duration of the stimulation cycle may all have some impact on the stimulation effect, which can be reflected in the evoked response of the muscles or other tissues through analysis of the second spinal cord image. Therefore, the second spinal cord image can further provide information for tuning the first imaging process and/or the stimulation process in the next stimulation cycle.

The difference between the intended stimulation and the actual stimulation can also be obtained by other means. In certain embodiments, the actual stimulation area is not determined directly. Instead the muscles innervated from the pre-determined stimulation area of the spinal cord are monitored. Likewise, a second spinal cord image can be used to analyze the muscle contraction. Other signals representing muscle contraction can also be collected. If the stimulation is applied to a wrong site or applied with less preferable parameters, the signal from the muscles cannot be well recorded. Alternatively, muscles at multiple places can be monitored so the actual stimulation area can be indirectly determined referring to the functional spinal cord mapping. This information can be relied on to adjust the first imaging process and/or the stimulation process in the next stimulation cycle.

With reference to FIG. 1, before the treatment, the patient has received prior diagnosis (step S0) and the area of the spinal cord to be stimulated is pre-determined. The treatment is implemented in a number of stimulation cycles. In each stimulation cycle, a first real-time spinal cord image is taken (step S1) in a first imaging process (steps S1-S3) using a first set of ultrasound transducers. The real-time spinal cord image can be two dimensional or three dimensional, depending on medical needs. The image will usually be of sufficient quality, either before or after pre-processing by an image processing filters, to enable subsequent selection. However, for some reasons of the apparatus or the patient, the quality of the image may not be satisfactory. In that case, a re-capture (step S11) can be done. If no image of satisfactory quality can be obtained, the treatment can be interrupted (step S12).

The first real-time spinal cord image is used for selecting a stimulation area of the spinal cord that corresponds with the pre-determined stimulation muscle/area of spinal cord in the prior diagnosis. Such selection can be done manually or automatically by an image recognition algorithm (step S2). The selection in the first cycle can be done manually and the selected stimulation area is loaded into the image recognition algorithm for training purpose. Alternatively, the image recognition algorithm can be generally or specifically trained in advance for the patient, and the selection from the first cycle can be performed automatically. Having selected the pre-determined stimulation area of spinal cord, the position and orientation of the selected stimulation area relative to a second set of ultrasound transducers for stimulating purpose can be calculated (step S3), with more details to be provided below. After learning the target stimulation area of the spinal cord, the second set of transducers can be configured with proper parameters to generate focused ultrasound beam directed to the target area to apply ultrasound stimulation (step S4).

Besides selection of stimulation area, many parameters of the ultrasound stimulation need to be configured. Non-limiting examples include focal area, focal point, intensity and frequency of the ultrasound beam, and the repetition rate, duty cycle and duration of each stimulation cycle. These parameters need to be optimized for each patient according to his or her injury or disease and physical conditions. An ultrasound signal of low intensity is generally preferred, as high intensity signals may overheat body tissue and cause necrosis. The range of low intensity can be determined with reference to US FDA standards and/or European Safety standards, and can be determined by doctors in accordance with each patient's circumstances. The frequency of ultrasound signal, for stimulating purpose, can be set at 0.25-5 MHz. In certain embodiments, the frequency of ultrasound signal, for stimulating purpose, can be set at 0.25-0.5 MHz, 0.5-0.75 MHz, 0.75-1 MHz, 1-1.5 MHz, 1.5-2 MHz, 2-2.5 MHz, 2.5-3 MHz, 3-3.5 MHz, 3.5-4 MHz, 4-4.5 MHz or 4.5-5 MHz Likewise, other parameters like repetition rate, duty cycle and duration of each stimulation cycle can be determined by doctors in accordance with each patient's circumstances. The duration of each cycle should be relatively short. It reduces impact of patient movement during the treatment and also risks of stimulation to wrong areas of spinal cord. Such short duration essentially makes the imaging and stimulation dynamic.

Also with reference to FIG. 1, in certain embodiments, immediately after the stimulation has been applied to the selected stimulation area in each stimulation cycle or while the stimulation is being applied to the selected pre-determined stimulation area in each stimulation cycle, a feedback process (steps S5-S6) is involved. In the feedback process, a second real-time spinal cord image will be taken in a second imaging process (or an ultrasound elasticity imaging process) (step S5). From the second real-time spinal cord image, the effectiveness of the stimulation can be evaluated (step S6). This includes, for instance, an evaluation whether the actual stimulation area is of the same location, contour and/or size of the pre-determined stimulation area. The determination is possible because a local tissue deformation and a local tissue vibration are induced by acoustic radiation force from the focused ultrasound beam. Such local tissue deformation and vibration can be detected by the ultrasound imaging (step S5). Ultra-fast imaging technique (over 2,000 frames per second) is usually required in this second imaging process. Methods other than ultrasound imaging can also be used (not shown). In certain embodiments, a signal representing muscle contraction from muscle innervated from the spinal cord stimulation area is taken. The signal comprises at least one of electromyography, sonomyography, mechanomyography, or electroneurography signal. The signal can help determining whether the pre-determined stimulation area is stimulated, and how effective is the stimulation. Alternatively, the signal can help determining indirectly the actual stimulation area of the spinal cord. In this way, the difference between intended stimulation and actual stimulation can be found out to see if the stimulation is applied accurately and/or effectively (step S6). In case there is any need of improvement, the information can be relied on to adjust the first imaging process (steps S1-S3) and/or stimulation process (step S4) in the next stimulation cycle. The adjustment comprises, for instance, optimizing the algorithm of selecting the pre-determined stimulation area, in particular improving the accuracy in selection of the pre-determined stimulation area; compensating the calculation of the relative orientation and position of the selected stimulation area to the second set of transducers for stimulating purposes, in particular compensating any errors that may come from the installation of the apparatus, the output of sensors, etc; and adjusting the focal point, focal area, intensity and frequency of the ultrasound beam; and the duty cycle, repetition rate and duration of each stimulation cycle. Other types of adjustments are also possible and within the contemplation of the present disclosure.

In a second stimulation cycle of the treatment, the pre-determined stimulation area will be re-selected and the position and orientation of the selected stimulation area relative to the second set of transducers will be re-calculated. If there is any difference between the intended stimulation and actual stimulation found in the first stimulation cycle, the feedback information can be taken into account to improve the re-selection and/or re-calculation and/or the parameters of the second set of transducers in the second stimulation cycle. Stimulation is then performed by the second set of transducers based on the improved processes and/or parameters based on a fresh first real-time spinal cord image. Again, further feedback and improvements can be done to the third stimulation cycle and all subsequent stimulation cycles. In this way, the risk of misapplication or improper application of ultrasound stimulation is minimized and the effect of stimulation can be optimized.

Figure 2:
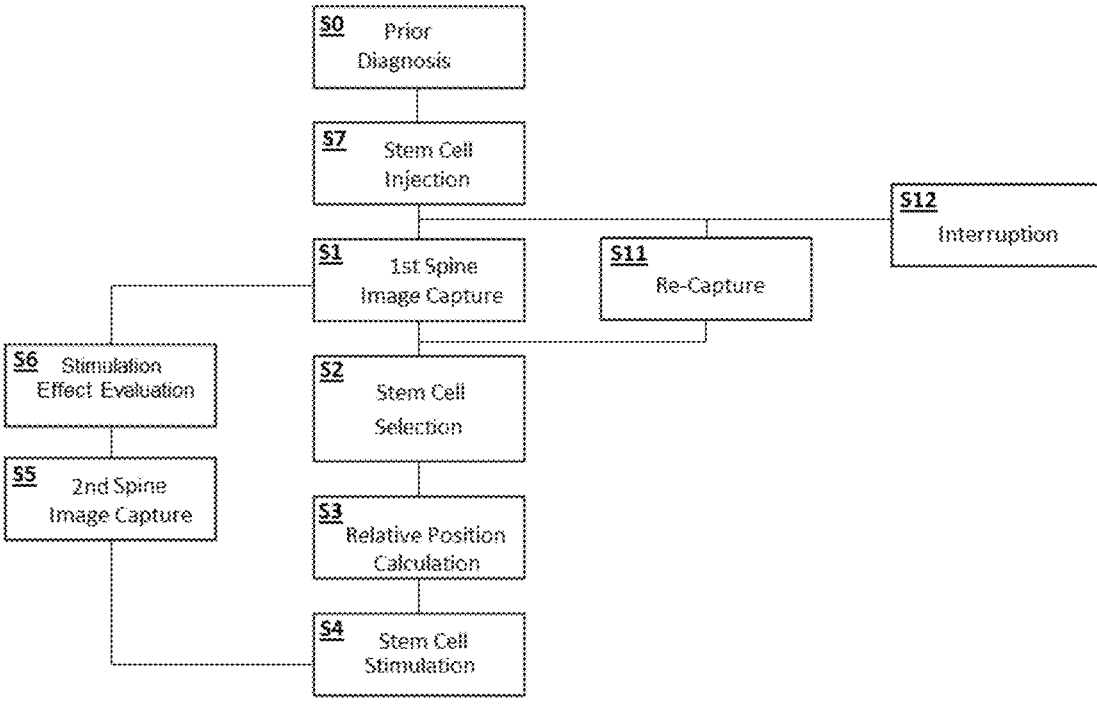
FIG. 2 illustrates a method for ultrasound stimulated rehabilitation of spinal cord injury or disease according to certain embodiments of the present disclosure.

In certain embodiments with reference to FIG. 2, the method relates to rehabilitation of paralyzing injury or disease with stem cells injection and activation. The substance of the method is similar to the previous stimulation method. In the prior diagnosis (step S0), the injury or disease is diagnosed and the damaged area of the spinal cord is determined. The method seeks to recover the damage by injecting stem cells thereto (step S7). Having injected the stem cells to the target area of the spinal cord, the stimulation method of the present disclosure can be relied on to activate the stem cells. In each working cycle, a first real-time spinal cord image is obtained using a first set of ultrasound transducers (step S1). The pre-determined stimulation area with the stem cells or the stem cells per se are selected from the first real-time spinal cord image (step S2). The ultrasound stimulations can then be applied to the selected stimulation area or the stem cells (steps S3 and S4). In certain embodiments, in each cycle, a feedback process (steps S5 and S6) is utilized to ensure the stem cells are properly stimulated and to adjust the location, intensity and/or other parameters of the ultrasound stimulation (steps S5 and S6) if needed. It should be noted the present method is not limited to rehabilitation of spinal cord injury or disease but can also be applied to rehabilitation of other injuries or diseases where stem cells are used and ultrasound stimulation is desired.

Figure 3:
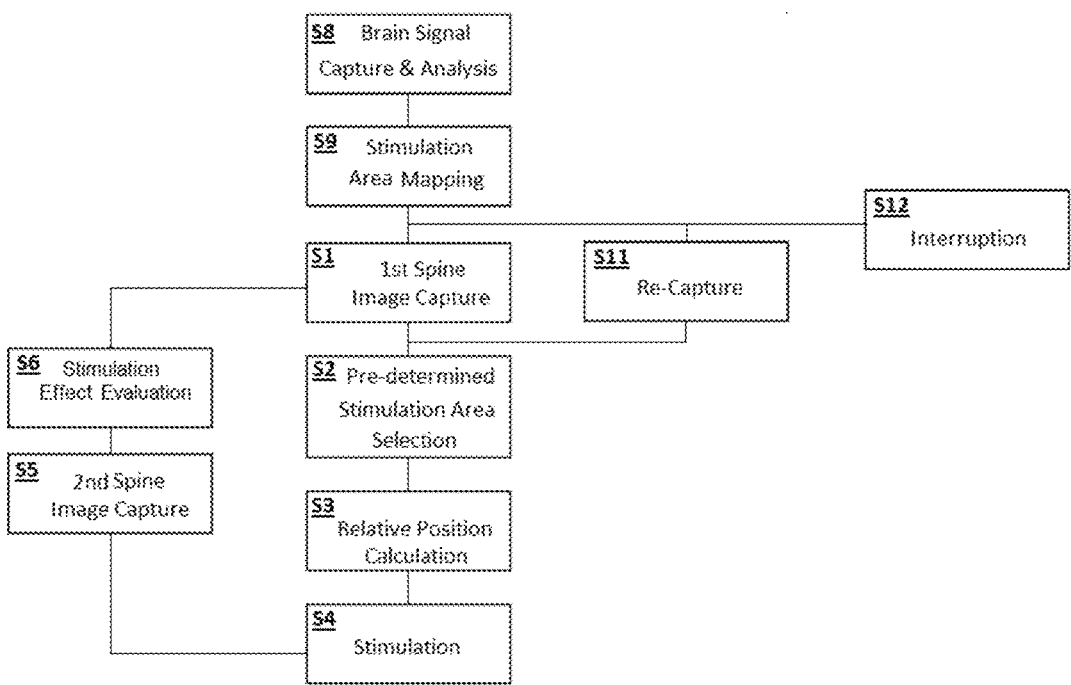
FIG. 3 illustrates a method for volitional triggering of a motor action according to certain embodiments of the present disclosure.

In certain embodiments with reference to FIG. 3, the method relates to bypassing the injured part of spinal cord and activating the intact part of spinal cord. There are situations where the paralyzing injury or disease of the spinal cord is so severe that there is little hope of rehabilitation. On the other hand, there are parts of spinal cord that are intact, only their communication with the brain is interrupted. The present method can be used in this scenario, not for rehabilitation purpose but for direct activation of the motor action or actions controlled by the intact parts of the spinal cord. To do so brain signal representing an intended motor action or actions is collected (step S8). The stimulation area of the spinal cord can be determined based on the signal with reference to an established functional mapping of spinal cord (step S9). Ultrasound stimulations can then be applied to such intact area of the spinal cord using the aforesaid stimulation method (steps S1 to S6) so that the motor action or actions can be activated. In this way, despite areas of spinal cord with severe damages cannot be rehabilitated, communication bypassing the damaged areas and to the other intact areas of the spinal cord can be established by the method of the present disclosure, so that motor action or actions modulated by these intact areas of the spinal cord can be restored. The signal collected from the brain comprises at least one of electroencephalogram (EEG), electrocorticography (ECoG), near-infrared spectroscopy, or brain vessel blood flow signal.

Figure 4:
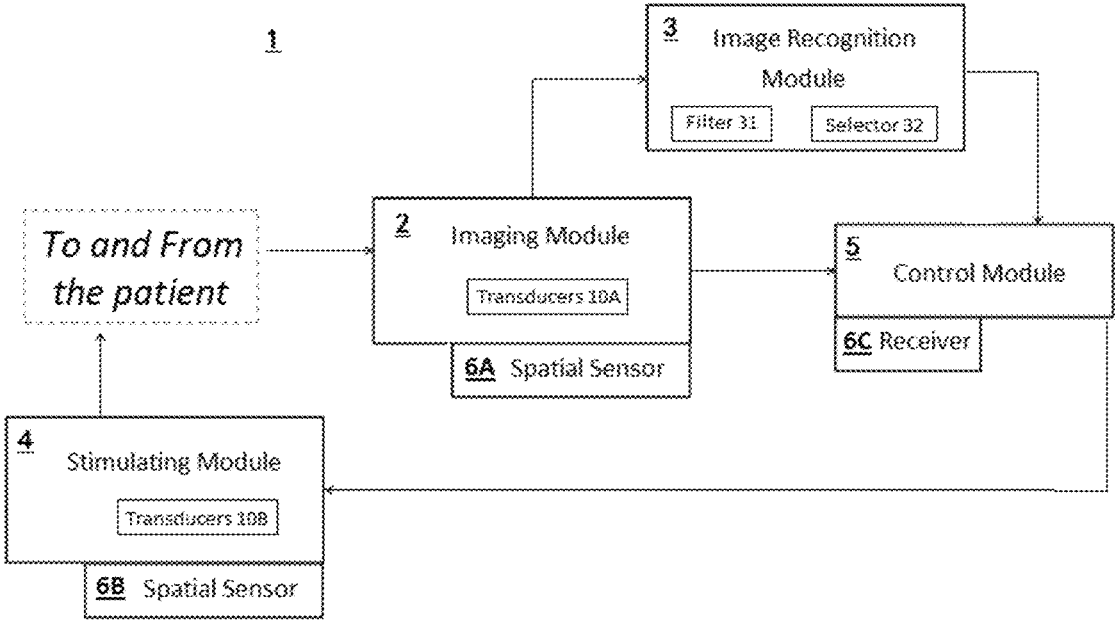
FIG. 4 illustrates an apparatus for ultrasound stimulation of spinal cord according to certain embodiments of the present disclosure.
Figure 7:
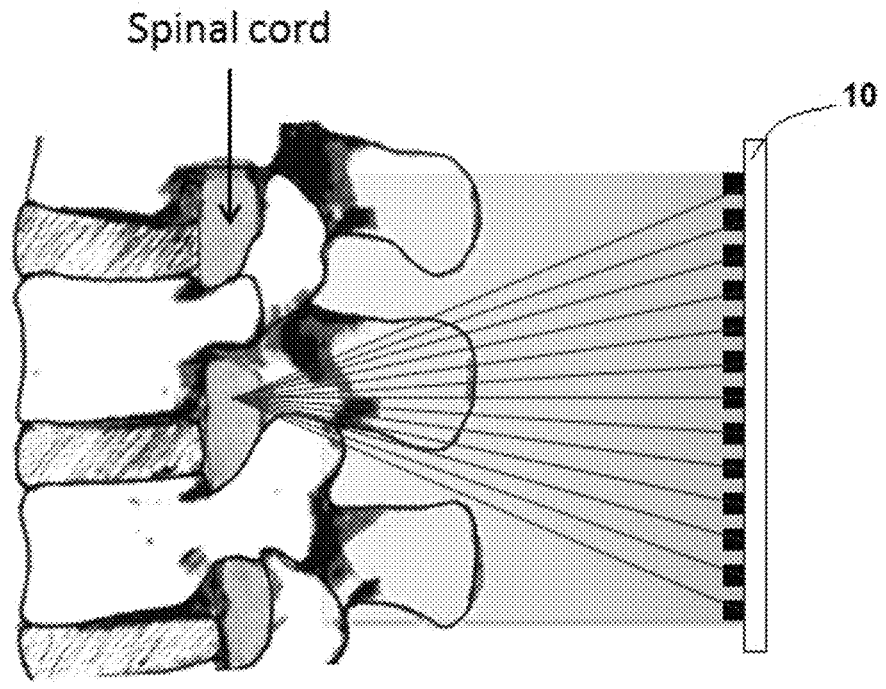
FIG. 7 illustrates a lateral view of spinal cord with ultrasound transducers of the apparatus according to certain embodiments of the present disclosure.
Figure 8:
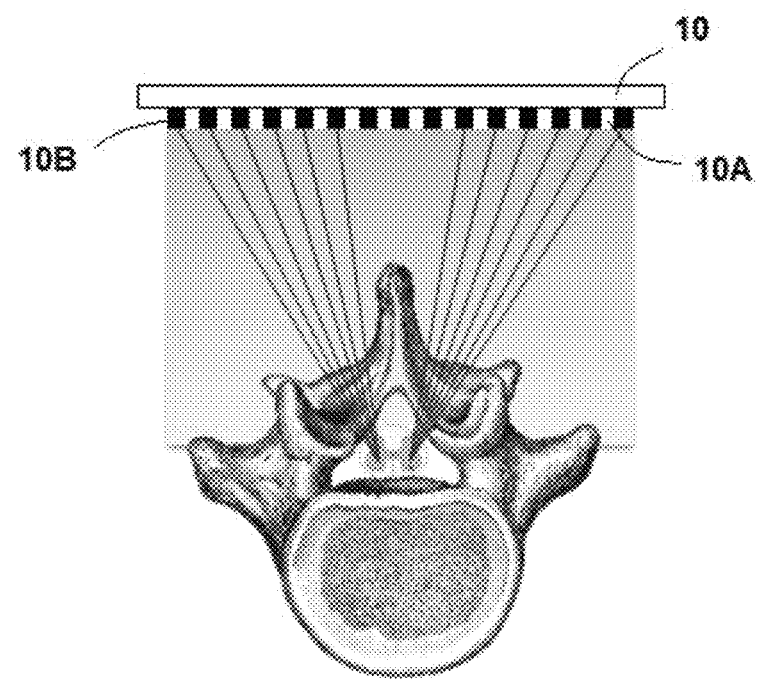
FIG. 8 illustrates an axial view of spinal cord with ultrasound transducers of the apparatus according to certain embodiments of the present disclosure.
Figure 9:
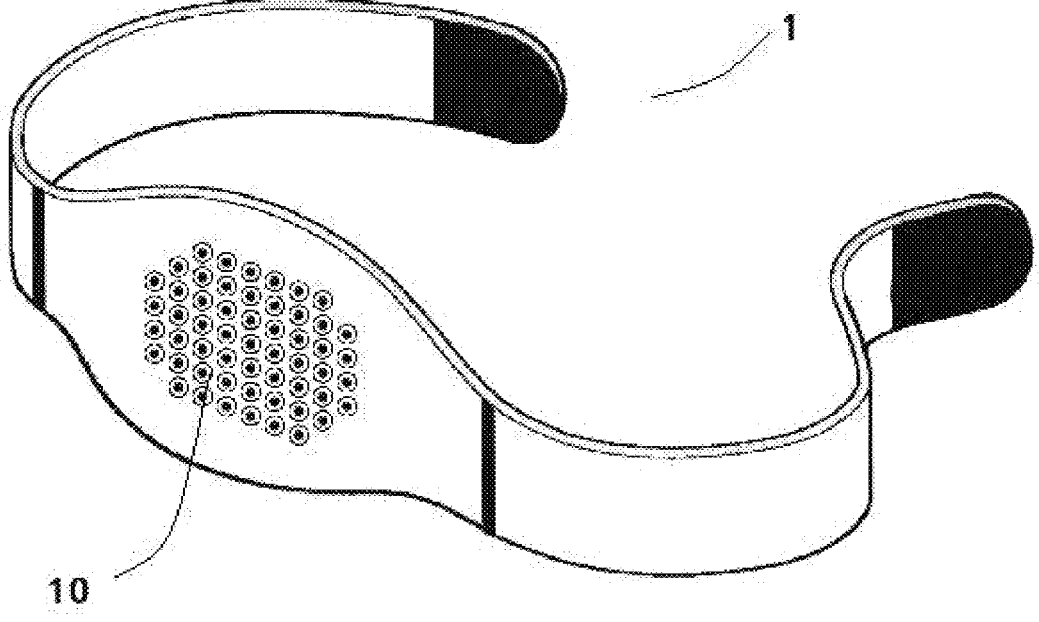
FIG. 9 illustrates an apparatus for ultrasound stimulation of spinal cord according to certain embodiments of the present disclosure in a wearable form.

With reference to FIG. 4, the apparatus 1 comprises an imaging module 2, an image recognition module 3, a stimulating module 4 and a control module 5. The apparatus 1 can be a platform type to be used at institutions, but it can also be miniaturized into a wearable and portable type. The control module 5 coordinates the working of the other modules and can include an interface for manual configuration, particularly for input of prior diagnosis data. The control module 5 can be a general personal computer, a palm device (including smartphone) or other tailor made device. Both the imaging module 2 and the stimulating module 4 comprise ultrasound transducers 10. In certain embodiments, the ultrasound transducers 10 of the imaging module 2 and the stimulating module 4 can be the same set (FIG. 7). The same set of transducers 10 can work in an imaging mode and a stimulating mode alternatively. In other embodiments, the imaging module 2 comprises a first set of transducers 10A and the stimulating module 4 comprises a second set of transducers 10B that is different from the first set of transducers 10A (FIG. 8). The first set of transducers 10A is exclusively for imaging and the second set of transducers 10B is exclusively for stimulation. The two sets of transducers 10A, 10B can be arranged separately or together. The other ways of arrangement are also possible and within the contemplation of the present disclosure. In certain embodiments, the transducers 10, 10A, 10B of the imaging module 2 and the stimulating module 4 are arranged on the same substrate forming an array for the convenience of arranging and locating the transducers relative to each other. The array can be one dimensional or two dimensional. The substrate can be a rigid one, or a flexible one as shown in FIG. 9 if the apparatus is intended to be worn on body, such that first and second sets of transducers 10A, 10B are located on the skin surface of patient in use.

The ultrasound transducers 10 can be of any type. As non-limiting examples, the ultrasound transducers 10 can be piezoelectric transducers, capacitive transducers, optoacoustic transducers, etc. For imaging purpose, it is preferred the ultrasonic signal is at the frequency range of 2.5-20 MHz; while for stimulation purpose, it is preferred the ultrasonic signal is at the frequency range of 0.25-5 MHz. There are other working parameters of the transducers 10 which will be addressed below.

A non-limiting example of the imaging module 2 is disclosed in another patent of the same applicant, U.S. Pat. No. 8,900,146 B2, the full content of which is incorporated herein by reference. When a one dimensional array of transducers 10A is used for the imaging module 2, a two dimensional spinal cord image can be obtained; when a two dimensional array of transducers 10A is used for the imaging module 2, a three dimensional spinal cord image can be obtained. The dimension of array largely depends on the geometry of the spinal cord tissue to be stimulated. The transducers 10A of the imaging module 2 take at least a first real-time spinal cord image in each stimulation cycle.

The image recognition module 3 is configured to select the pre-determined stimulation area from the first real-time spinal cord image for each stimulation cycle. In certain embodiments, it is not necessary for the image recognition module 3 to be a separate and independent module, the selection of stimulation area can be done by the image module 2 or the control module 5. As the spinal cord image can be captured in two or three dimensions, the image recognition module 3 is able to select two or three dimensional stimulation areas accordingly. In certain embodiments, the captured images can be preprocessed by various kinds of image processing filters 31, such as pseudo color coding, to enhance the image quality and contrast. The pre-determined stimulation area can then be selected manually or automatically by a selector 32. In certain embodiments the selection is done automatically by an advanced image recognition algorithm so that the time interval between image capture by the imaging module 2 and the stimulation by the stimulating module 4 is reduced to minimize the risk of wrongful stimulation. The image recognition algorithm is trained in advance so it has a reasonable accuracy in identifying the pre-determined stimulation areas of the patient's spinal cord. An image or images with manual selection of the pre-determined stimulation area can be loaded into the image recognition module 3 for training before each treatment. The image recognition algorithm, in certain embodiments, will also be improved in the subsequent stimulation cycles with feedback information.

Having selected the pre-determined stimulation area of the spinal cord, the image recognition module 3 can further locate the position and orientation of the selected stimulation area relative to the transducers 10A of the imaging module 2, which can be represented by a first rigid transform matrix. Generally, the position and orientation of the transducers 10A of the imaging module 2 relative to the transducers 10B of the stimulating module 4 are fixed and known, which can be represented by a second rigid transform matrix. As previously discussed, the transducers 10 of the imaging module 2 and the stimulating module 4 can be of the same set. If they are two different sets, the transducers 10A, 10B can be arranged on the same substrate in a known manner to form an array. However, it is also possible to learn the relative position and orientation even if the transducers 10A, 10B of the imaging module 2 and the stimulating module 4 are arranged separately. In this scenario, a first spatial sensor 6A can be attached to the imaging module 2, a second spatial sensor 6B can be attached to the stimulating module 6, and a receiver 6C can be attached to the control module 5 or any other reference position. The receiver 6C generates a magnetic field in space, the spatial sensors 6A, 6B sense the strength of magnetic field and the change of magnitude of the magnetic filed. The results are processed to calculate the position and orientation of each spatial sensor 6A, 6B relative to the receiver 6C. As such, the relative position and the orientation of the first and second spatial sensors 6A, 6B, and consequently the relative position and orientation of the transducers 10A of the imaging module 2 and the transducers 10B of the stimulating module 4 (i.e. the second rigid transform matrix) can be calculated. For accuracy, the spatial sensors 6A, 6B and the receiver 6C can be calibrated prior to each use. With the first and second rigid transform matrixes known, the position and orientation of the selected stimulation area relative to the transducers 10B of the stimulating module 4 can be calculated. In certain embodiments, there can be a further third rigid transform matrix in the calculation of relative position and orientation between the selected stimulation area of the spinal cord and the second set of transducers 10B. This third rigid transform matrix is intended to compensate any misalignment, error or other sources of inaccuracy in the calculation. The third rigid transform matrix can be defined in the feedback process.

The stimulating module 4, as discussed above, comprises a second set of transducers 10B arranged in an array. Once the position and orientation of the stimulation area of the spinal cord relative to the transducers 10B are known, the transducers 10B can generate pulsed ultrasounds to create a focused ultrasound beam directed to the stimulation area as shown in FIG. 7. In certain embodiments, the ultrasound beam reaches the spinal cord by passing through the gap between vertebral bones and the lamina. In certain embodiments, if more than one stimulation area is desired, the transducers can be configured such that they can perform multifocal stimulation simultaneously as shown in FIG. 8. In other words, the transducers simultaneously activate multiple muscle groups required for a motion function. This is particularly essential to activate agonist muscles that operate at the same time to execute a motor task. The focusing of the ultrasound signals from the multiple transducers 10B can be done in many ways. For instance, the second set of transducers 10B can be mechanically moved (e.g. by rotation or translation) to change the focal area. A more preferred way is by electronic focusing. The pulsed ultrasounds at different delays from each transducer are utilized to create the focused ultrasound beam.

The imaging module 2 and the image recognition module 3 also wok in a feedback process, as coordinated by the control module 5. In particular, the control module 5 coordinates the imaging process, the stimulation process and the feedback process. The details of which have been discussed above.

Figures 5, 6:
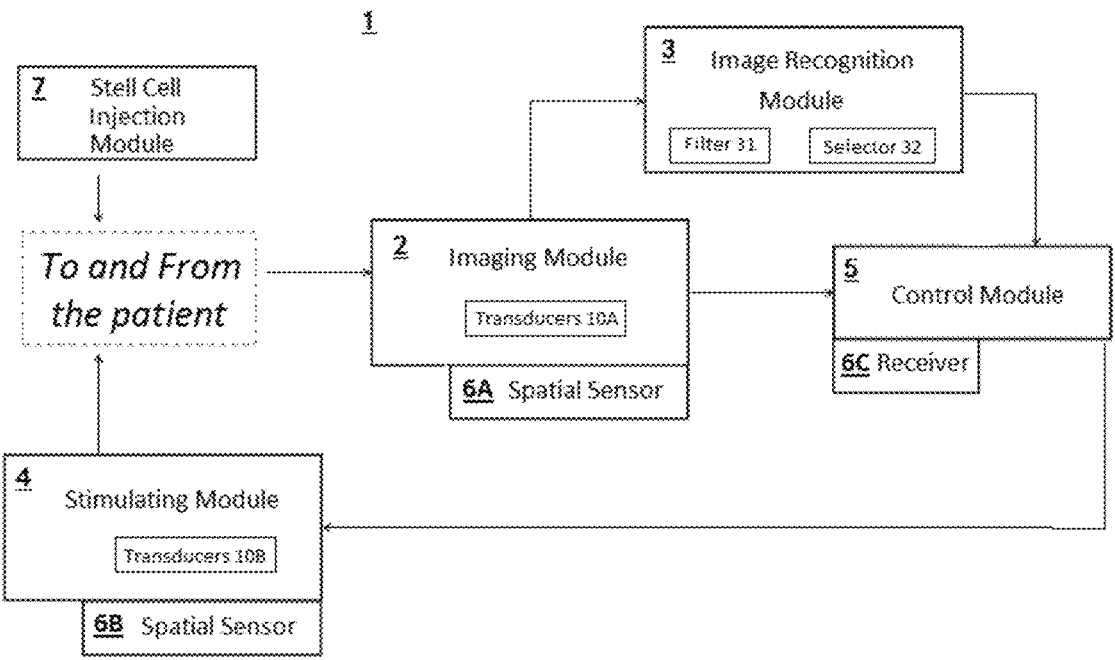
FIG. 5 illustrates an apparatus for ultrasound stimulated rehabilitation of spinal cord injury or disease according to certain embodiments of the present disclosure.
FIG. 6 illustrates an apparatus for volitional triggering of a motor action according to certain embodiments of the present disclosure.

In certain embodiments as shown in FIG. 5, the apparatus 1 further comprises a stem cell injection module 7. Alternatively, the stem cell injection module 7 can be a separate system to be used in association with the apparatus 1 of the present disclosure. The stem cell injection module 7 is provided to inject stem cells to an impaired area of the spinal cord. This impaired area is pre-determined in a prior diagnosis. The imaging module 2 and the image recognition module 3 can then be used to identify and locate the pre-determined area or the stem cells and the stimulating module 4 can then be used to stimulate the pre-determined area or the stem cells in vivo to activate the stem cells and to improve the rehabilitation of the paralyzing injury or disease.

In certain embodiments as shown in FIG. 6, the apparatus 1 comprises a brain signal receiving module 8 for receiving brain signals from the brain of patient. The brain signal receiving module 8 is in communication with the control module 5 so that the collected signal is sent to the control module 5 for further processing. The brain signal represents an intended motor action or actions. The stimulation area of the spinal cord can be determined by the brain signal receiving module 8 or the control module 5 based on the signal with reference to an established functional mapping of spinal cord. As such, the corresponding stimulation area of the spinal cord can be applied with ultrasound stimulation to start the intended motor action or actions.

Although this disclosure has been described in terms of certain embodiments, other embodiments apparent to those of ordinary skill in the art are also within the scope of this disclosure. Accordingly, the scope of the disclosure is intended to be defined only by the claims which follow.

What is claimed is:

1. A method for ultrasound stimulation of a spinal cord by an apparatus, the method comprising at least two stimulation cycles, each comprising the steps of:
    a) obtaining a first real-time spinal cord image using a first set of ultrasound transducers;
    b) selecting a pre-determined stimulation area of the spinal cord from the first real-time spinal cord image;
    c) calculating a position and orientation of the selected stimulation area relative to a second set of ultrasound transducers; and
    d) stimulating the selected stimulation area of the spinal cord at the calculated relative position and orientation using the second set of ultrasound transducers,
    wherein the apparatus comprises:

an imaging module, wherein the imaging module comprises the first set of ultrasound transducers configured to obtain real-time spinal cord images;
    an image recognition module, wherein the image recognition module is configured to select the pre-determined stimulation area of the spinal cord from the first real-time spinal cord image of the real-time spinal cord images, and to calculate a position and orientation of the selected stimulation area relative to the first set of ultrasound transducers represented by a first rigid transform matrix;
    a stimulating module, wherein the stimulating module comprises the second set of ultrasound transducers configured to stimulate the selected stimulation area of the spinal cord at the calculated relative position and orientation subsequent to the selection of the pre-determined stimulation area of the spinal cord from the first real-time spinal cord image; and
    a control module, wherein the control module is configured to coordinate the imaging module, the image recognition module and the stimulating module to operate in at least two stimulation cycles, and wherein in each of the at least two stimulation cycles, at the same time of or after ultrasound stimulation is applied to the selected stimulation area of the spinal cord by the stimulating module, the following actions are performed:
        the imaging module obtains a second real-time spinal cord image;
        the image recognition module recognizes an actual stimulation area of the spinal cord from the second real-time spinal cord image; and
        the control module adjusts the recognition module and/or the stimulating module based on a difference between the actual stimulation area and the pre-determined stimulation area;
    wherein:
    the control module further comprises a receiver configured to generate a magnetic field in space;
    the imaging module further comprises a first spatial sensor configured to sense the magnetic field;
    the stimulating module further comprises a second spatial sensor configured to sense the magnetic field;
    the image recognition module is further configured to calculate a position and orientation of the first and second spatial sensors relative to the receiver according to a strength of the magnetic field and a change of magnitude of the magnetic field, to thereby calculate a position and orientation of the first set of ultrasound transducers relative to the second set of ultrasound transducers represented by a second rigid transform matrix; and
    the image recognition module is further configured to calculate the position and orientation of the selected stimulation area relative to the second set of ultrasound transducers with the first and second rigid transform matrixes.

2. The method of claim 1, each stimulation cycle further comprising the steps of:
    e) at the same time of or after step d), obtaining a second real-time spinal cord image using the first set of ultrasound transducers;
    f) recognizing an actual stimulation area of the spinal cord from the second real-time spinal cord image; and
    g) adjusting at least one of steps b) to d) based on the difference between the actual stimulation area and the pre-determined stimulation area.

3. The method of claim 2, wherein the difference comprises a difference in location, contour and/or size between the actual stimulation area and the pre-determined stimulation area.

4. The method of claim 2, wherein the difference comprises an evoked response of a muscle at the actual stimulation area.

5. The method of claim 2, wherein adjusting step b) comprises optimizing an image recognition algorithm for selecting the pre-determined stimulation area of the spinal cord from the first real-time spinal cord image.

6. The method of claim 2, wherein adjusting step c) comprises compensating the calculation of the position and orientation of the selected stimulation area relative to the second set of ultrasound transducers.

7. The method of claim 2, wherein adjusting step d) comprises adjusting at least one of focus point, focus area, intensity and frequency of an ultrasound beam, and duty cycle, repetition rate and duration of the stimulation cycle.

8. The method of claim 2, wherein the second real-time spinal cord image is taken by the first set of ultrasound transducers at a rate over 2,000 frames per second.

9. The method of claim 1, each stimulation cycle further comprising the steps of:
h) at the same time of or after step d), collecting a signal representing muscle contraction from muscle innervated from the pre-determined stimulation area of the spinal cord; and
i) adjusting at least one of steps b) to d) based on the signal.

10. The method of claim 9, wherein the signal comprises at least one of electromyography, sonomyography, mechanomyography, or electroneurography signal.

11. The method of claim 9, wherein adjusting step b) comprises optimizing an image recognition algorithm for selecting the pre-determined stimulation area of the spinal cord from the first real-time spinal cord image.

12. The method of claim 9, wherein adjusting step c) comprises compensating the calculation of the position and orientation of the selected stimulation area relative to the second set of ultrasound transducers.

13. The method of claim 9, wherein adjusting step d) comprises adjusting at least one of focus point, focus area, intensity and frequency of an ultrasound beam; and duty cycle, repetition rate and duration of the stimulation cycle.

14. The method of claim 1, wherein step b) comprises the step of selecting multiple pre-determined stimulation areas of the spinal cord, and step d) comprises the step of simultaneous multifocal stimulation of the multiple selected stimulation areas of the spinal cord, so as to simultaneously activate multiple muscle groups required for a motion function.

15. The method of claim 1, wherein in step d) an ultrasound beam of the second set of transducers reaches the selected stimulation area of the spinal cord by passing through a gap between vertebral bones and a lamina.

16. The method of claim 1 further comprising: injecting stem cells in the pre-determined area of the spinal cord prior to step a) obtaining the first real-time spinal cord image using the first step of ultrasound transducers; and step d) stimulating the selected stimulation area of the spinal cord stimulates the stem cells.

* * * * *